United States Patent
Freehauf et al.

(10) Patent No.: US 10,045,940 B2
(45) Date of Patent: Aug. 14, 2018

US010045940B2

(54) COMPOSITION COMPRISING AN ANTIBIOTIC AND A CORTICOSTEROID

(75) Inventors: Keith A. Freehauf, Summit, NJ (US); Jay Brumfield, Summit, NJ (US); Roger Tully, Mildenhall (GB)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 13/286,747

(22) Filed: Nov. 1, 2011

(65) Prior Publication Data

US 2012/0046259 A1 Feb. 23, 2012

Related U.S. Application Data

(62) Division of application No. 12/476,783, filed on Jun. 2, 2009, now abandoned.

(60) Provisional application No. 61/057,940, filed on Jun. 2, 2008.

(51) Int. Cl.

| | |
|---|---|
| *A61K 31/496* | (2006.01) |
| *A61K 31/50* | (2006.01) |
| *A61K 31/58* | (2006.01) |
| *A61K 9/10* | (2006.01) |
| *A61K 9/00* | (2006.01) |
| *A61K 45/06* | (2006.01) |
| *A61K 47/12* | (2006.01) |
| *A61K 9/14* | (2006.01) |

(52) U.S. Cl.
CPC .............. *A61K 9/10* (2013.01); *A61K 9/0046* (2013.01); *A61K 31/496* (2013.01); *A61K 31/58* (2013.01); *A61K 45/06* (2013.01); *A61K 47/12* (2013.01); *A61K 9/14* (2013.01)

(58) Field of Classification Search
CPC ....... A61K 31/50; A61K 31/58; A61K 30/496
See application file for complete search history.

(56) References Cited

U.S. PATENT DOCUMENTS

| | | | |
|---|---|---|---|
| 6,416,743 B1* | 7/2002 | Fassberg et al. ................ 424/45 |
| 8,697,751 B2* | 4/2014 | Sakai ................... A61K 31/5575 |
| | | | 514/573 |
| 2006/0122159 A1* | 6/2006 | Huq et al. ....................... 514/171 |
| 2007/0196398 A1* | 8/2007 | Murthy ........................... 424/400 |
| 2008/0253970 A1* | 10/2008 | Sherwood .............. A61K 9/008 |
| | | | 424/45 |
| 2011/0034478 A1* | 2/2011 | Fang ...................... A61K 9/1652 |
| | | | 514/254.07 |

FOREIGN PATENT DOCUMENTS

| | | |
|---|---|---|
| RU | 2201219 C2 | 3/2003 |
| RU | 2267491 C1 | 1/2006 |
| WO | 2000068243 A1 | 11/2000 |
| WO | WO 03/000175 | 1/2003 |
| WO | WO 2006/020689 | 2/2006 |
| WO | WO 2007/064912 * | 6/2007 |
| WO | 2008063341 A2 | 5/2008 |

OTHER PUBLICATIONS

Morimura et al. Degradation kinetics of the new antibacterial fluoroquinolone derivative, orbiflaxacin, in aqueous solution. Chem. Pharm. Bull. 43(6), 1052-1054, 1995.*
Vippagunta et al., "Crystalline solids", Advanced Drug Delivery Reviews, 2001, pp. 3-26, vol. 48.
Tsuji et al., "Pharmaceutical Properties of Freeze-Dried Formulations of Egg Albumin, Several Drugs and Olive Oil", Biological & Pharmaceutical Bulletin of Japan, 1996, pp. 636-640, vol. 19(4).
Shikov et al., Vegetable oils and oil extracts, Olive Oil, Found at Aromarti.ru forum, pp. 1-3, Aug. 26, 2008.

* cited by examiner

*Primary Examiner* — Shirley V Gembeh

(57) ABSTRACT

This invention relates to compositions (e.g., otic compositions) comprising an antibiotic (generally a quinolone or naphthyridinone), corticosteroid, and organic acid (generally a fatty acid). This invention also relates to treatment methods using such a composition, uses of such a composition to make medicaments, and therapeutic kits comprising such a composition.

12 Claims, No Drawings

COMPOSITION COMPRISING AN ANTIBIOTIC AND A CORTICOSTEROID

FIELD OF THE INVENTION

This invention relates to compositions comprising an antibiotic (generally a quinolone or naphthyridinone), corticosteroid, and organic acid (generally a fatty acid). This invention also relates to treatment methods using such a composition, uses of such a composition to make medicaments, and therapeutic kits comprising such a composition.

BACKGROUND OF THE INVENTION

US Patent Application Publication No. 2006-0122159 discusses pharmaceutical formulations useful for treating infections in animals, particularly otic infections. The compositions are generally described as comprising a corticosteroid, antibiotic, and triazole. They include, for example, suspensions comprising mometasone furoate monohydrate, orbifloxacin, and posaconazole. A specific formulation illustrated in US Patent Application Publication No. 2006-0122159 is shown in Table 1:

TABLE 1

Formulation from Example 1 in US Patent Appl. Publ. No. 2006-0122159

| Ingredient | mg/g |
| --- | --- |
| Micronized Orbifloxacin | 10.0 |
| Micronized Mometasone Furoate Monohydrate | 1.0 |
| Micronized Posaconazole | 1.0 |
| Mineral Oil USP (40 centistokes) | 685.0 |
| Plasticized Hydrocarbon Gel - Ointment Base (PLASTIBASE ® 50W, which is 5% polyethylene and 95% mineral oil) | quantity sufficient to bring the total mass to 1 g |

Applicants have observed an increase in at least one mometasone degradation product over time when the above formulation is stored at room temperature. Applicants have further observed that the orbifloxacin in the formulation accelerates the formation of the degradation product. The formation of the degradation product generally can be minimized by storing the formulation at colder temperatures (e.g., 5° C.). There is, however, a need for a formulation that can remain stable at greater temperatures (e.g., room temperature). This invention provides such a formulation.

SUMMARY OF THE INVENTION

Briefly, this invention is generally directed to compositions (e.g., suspensions) that comprise a corticosteroid and an antibiotic. These compositions generally are stable at room temperature or greater (e.g., at 50° C.) over an extended time (e.g., 5 months). Advantages of such stable compositions typically include, for example, elimination of the expense and manpower associated with refrigeration, elimination of the risk of product loss due to refrigeration failure, and elimination of the risk of degraded product being administered after inadvertent storage without refrigeration.

This invention, therefore, is directed, in part, to a pharmaceutical composition. The composition comprises a corticosteroid, an antibiotic, and an organic acid. The organic acid generally comprises a fatty acid that, in turn, comprises from about 3 to about 18 carbon atoms, and has a inciting point of no greater than about 60° C. In some embodiments, the antibiotic comprises a quinolone (particularly a fluoroquinolone, a salt of the fluoroquinolone, or a solvate of the fluoroquinolone or its salt). In other embodiments, the antibiotic comprises a naphthyridinone (particularly a fluoronaphthyridinone, a salt of the fluoronaphthyridinone, or a solvate of the fluoronaphthyridinone or its salt).

This invention also is directed, in part, to a method for treating an infection in an animal by administering an above-described composition to the animal.

This invention also is directed, in part, to a use of an above-described composition to prepare a medicament for treating an infection in an animal.

This invention also is directed, in part, to a therapeutic kit. The kit comprises an above-described composition and an additional component. The additional component may be, for example, a diagnostic tool, an otic cleaning solution, an apparatus for cleaning an ear, instructions for administering the composition to an animal, or a device for administering the composition to an animal.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

I. The Composition

The pharmaceutical composition of this invention generally comprises a corticosteroid, an antibiotic, and an organic acid. At the outset, it should be recognized that this list of ingredients is not exhaustive. The composition, therefore, may (and generally will) contain additional ingredients. These additional ingredients may include, for example, one or more additional corticosteroids, antibiotics, and/or organic acids. Also, as will be discussed in more detail below, the additional ingredients may comprise one or more other active ingredients. And, as will also be discussed below, the additional ingredients may (and generally will) comprise one or more excipients.

In general, the composition may be in various forms, particularly non-solid forms. For example, the composition may be in the form of a suspension, solution, emulsion, ointment, etc. In some embodiments, the composition is in the form of a suspension.

A. The Corticosteroid

Corticosteroids are generally natural and synthetic analogues of hormones secreted by the hypothalamic-anterior pituitary-adrenocortical axis (also known as the pituitary gland). Corticosteroids (particularly glucocorticoids) are generally known to be potent anti-inflammatory agents. They also typically show antipruritic and vasoconstrictive activity. Various corticosteroids are, for example, used topically to treat corticosteroid-responsive dermatoses, such as psoriasis and atopic dermatitis.

Examples of corticosteroids include the compounds shown in Table 2 (as well as salts of the compounds, and solvates of the compounds and salts):

TABLE 2
| Corticosteroid | Examples of reported trade names for products containing the corticosteroid | Structure |
| --- | --- | --- |
| beclomethasone dipropionate | BECLOVENT® QVAR® Vanceril | 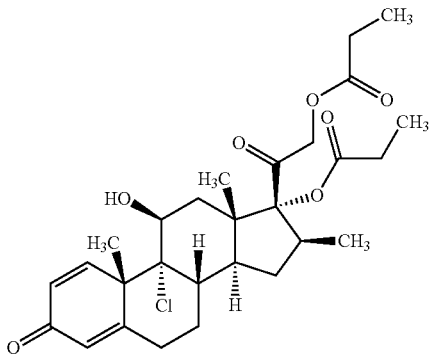 |
| betamethasone diproprionate | DIPROSONE DIPROLENE® | 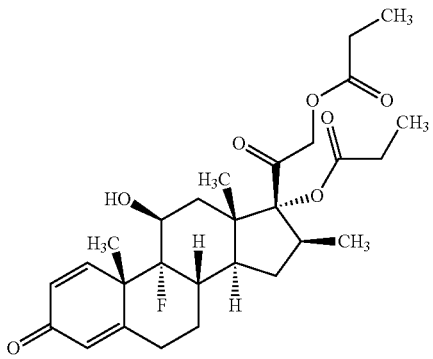 |
| betamethasone valerate | CELESTONE® M BETNOVATE® | 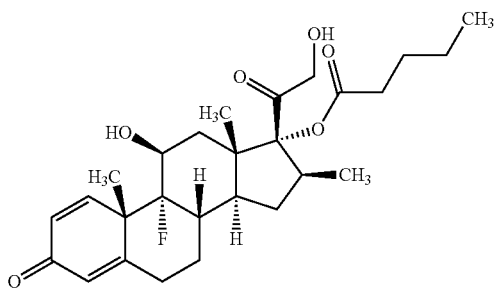 |
| budesonide | ENTOCORT® EC RHINOCORT AQUA® | 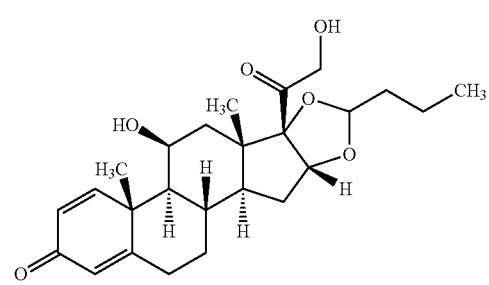 |

TABLE 2-continued
Examples of Corticosteroids
| Corticosteroid | Examples of reported trade names for products containing the corticosteroid | Structure |
|---|---|---|
| ciclesonide | ALVESCO® OMNARIS® | 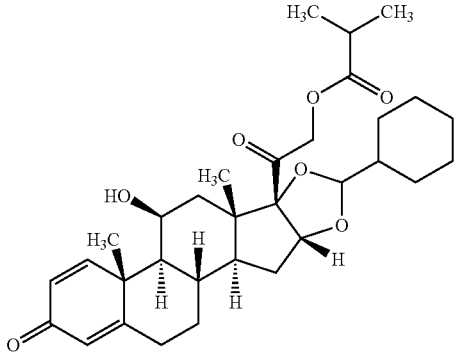 |
| deflazacort | CALCORT | 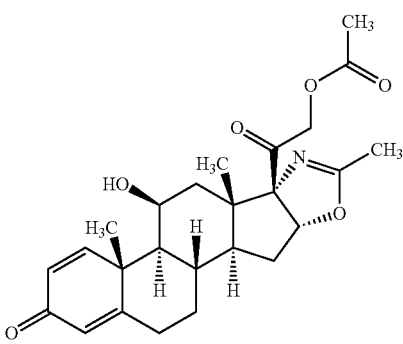 |
| dexamethasone | AZIUM® DEXACORT DECADRON® | 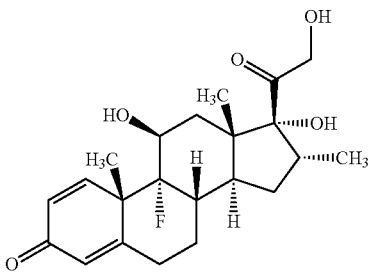 |
| fluocinolone acetonide | DERMA-SMOOTHE/FS RETISERT® | 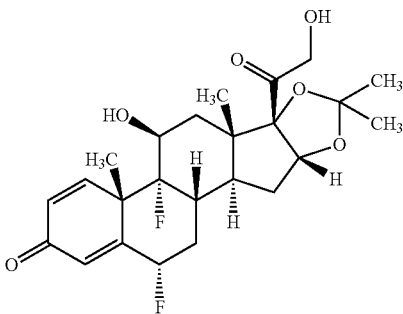 |

TABLE 2-continued
Examples of Corticosteroids
| Corticosteroid | Examples of reported trade names for products containing the corticosteroid | Structure |
|---|---|---|
| fluticasone propionate | FLIXOTIDE FLOVENT® FLIXONASE | 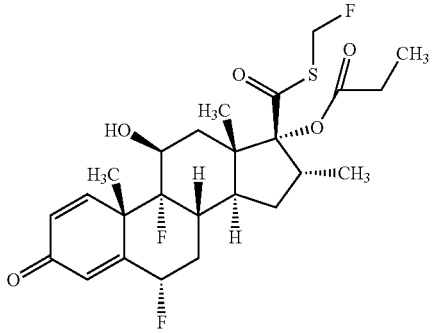 |
| fluticasone furoate | VERAMYST® | 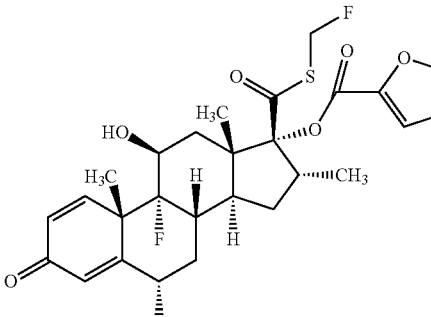 |
| loteprednol etabonate | ALREX® LOTEMAX® | 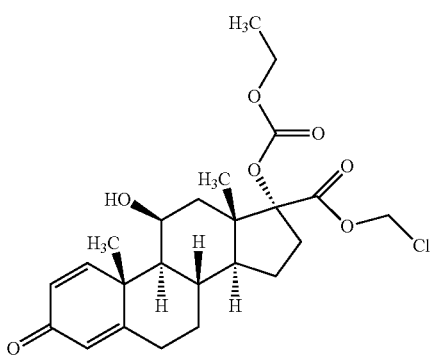 |
| Methylprednisolone | MEDROL® | 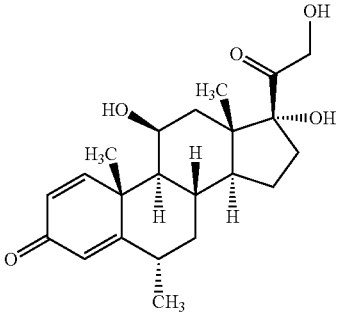 |

TABLE 2-continued

Examples of Corticosteroids

| Corticosteroid | Examples of reported trade names for products containing the corticosteroid | Structure |
| --- | --- | --- |
| prednisolone | PRELONE® METI-DERM | 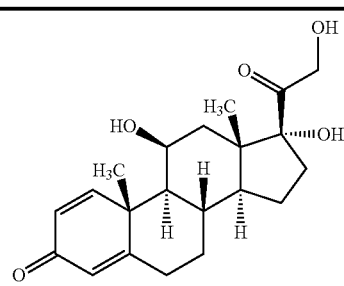 |
| prednisone | DELTASONE ORASONE® METICORTEN | 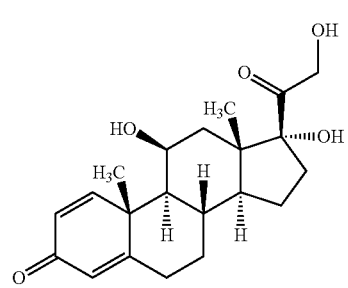 |
| rofleponide | | 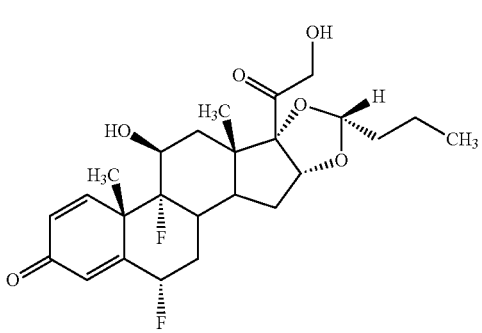 |
| triamcinolone acetonide | NASACORT® TRICORTONE | 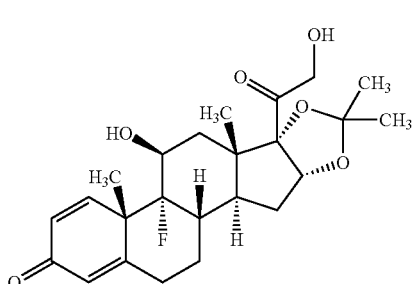 |

In some embodiments, the corticosteroid in the composition comprises a corticosteroid selected from the group consisting of the compounds in Table 2, their salts, and solvates of the compounds and their salts.

In other embodiments, the corticosteroid comprises mometasone, a salt of mometasone, or a solvate of mometasone or a mometasone salt. Mometasone is a synthetic glucocorticoid, and corresponds in structure to:

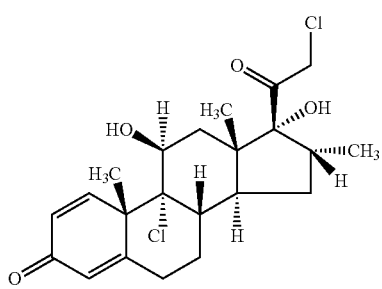

In other embodiments, the corticosteroid comprises a mometasone ester, a salt of a mometasone ester, or a solvate of a mometasone ester or mometasone ester salt. In some such embodiments, the mometasone ester comprises mometasone furoate. Mometasone furoate corresponds in structure to:

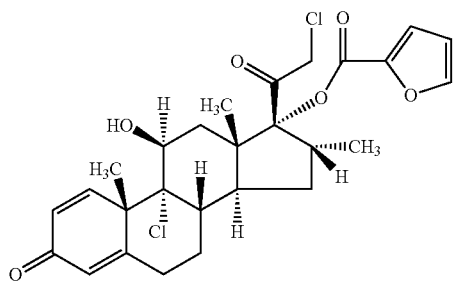

Its chemical name is 9,21-dichloro-11(beta),17-dihydroxy-16(alpha)-methylpregna-1,4-diene-3,20-dione 17-(2 furoate). Mometasone furoate is, for example, the active component of Elocon® lotion, cream, and ointment, and is commercially available from Schering-Plough Corporation (Kenilworth, N.J.).

Corticosteroids can exist in various enantiomeric forms. They also can exist in various crystalline forms. For example, as indicated above, a solvate of mometasone furoate may be used. In some embodiments, for example, the solvate comprises a hydrate. This hydrate may be, for example, the monohydrate.

In some embodiments, the corticosteroid comprises mometasone, mometasone furoate, or a solvate of mometasone or mometasone furoate (e.g., mometasone furoate monohydrate).

In general, the total corticosteroid concentration in the composition is sufficient for the corticosteroid to be therapeutically effective at the dose in which the composition is administered. In some embodiments, the total concentration of corticosteroid (e.g., mometasone, mometasone furoate, and/or solvate of mometasone or mometasone furoate) in the composition is at least about 0.01% (by weight). In some such embodiments, for example, the total concentration is from about 0.01 to about 1.0% (by weight).

B. The Antibiotic

In some embodiments, the antibiotic comprises a quinolone. In general, the quinolone comprises a fluoroquinolone, a salt of the fluoroquinolone, or a solvate of the fluoroquinolone or its salt. Fluoroquinolone antibiotics include, for example, 6-fluoroquinolin-4(1H)-ones, salts of 6-fluoroquinolin-4(1H)-ones, and solvates of 6-fluoroquinolin-4(1H)-ones and their salts. Examples of 6-fluoroquinolin-4(1H)-ones include those shown in Table 3:

TABLE 3

Examples of 6-Fluoroquinolin-4(1H)-ones

| 6-Fluoroquinolin-4(1H)-one | Examples of reported trade names for products containing the 6-fluoroquinolin-4(1H)-one | Structure |
| --- | --- | --- |
| amifloxacin | | 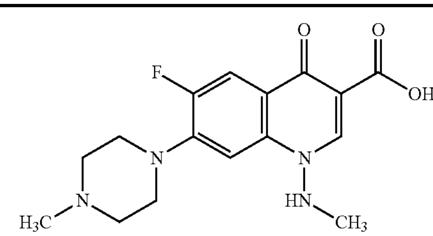 |
| balofloxacin | | 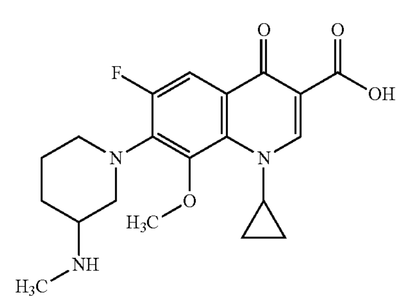 [SMILES: CNC1CCCN(c2c(F)cc3c(=O)c(C(=O)O)cn(C4CC4)c3c2OC)C1] |

TABLE 3-continued

Examples of 6-Fluoroquinolin-4(1H)-ones

| 6-Fluoroquinolin-4(1H)-one | Examples of reported trade names for products containing the 6-fluoroquinolin-4(1H)-one | Structure |
| --- | --- | --- |
| ciprofloxacin | CIPRO®, CIPROBAY, & CIPROXIN | 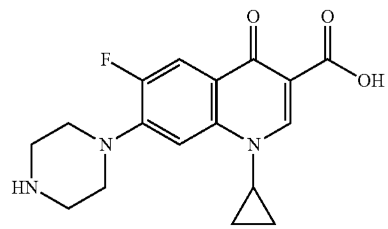 [SMILES: O=C(O)c1cn(C2CC2)c2cc(N3CCNCC3)c(F)cc2c1=O] |
| clinafloxacin | | 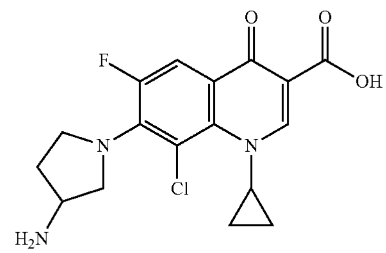 [SMILES: NC1CCN(c2c(F)cc3c(=O)c(C(=O)O)cn(C4CC4)c3c2Cl)C1] |
| danofloxacin | ADVOCIN & ADVOCID | 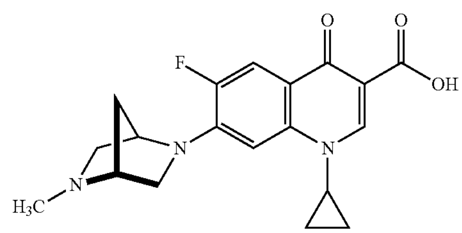 |
| difloxacin | DICURAL® & VETEQUINON | 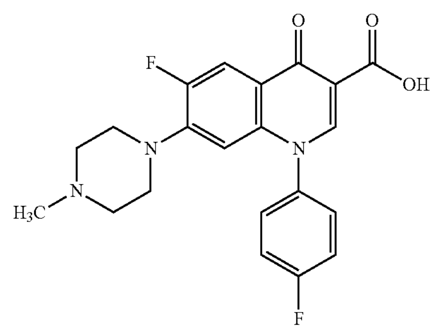 [SMILES: CN1CCN(c2cc3c(cc2F)c(=O)c(C(=O)O)cn3-c2ccc(F)cc2)CC1] |
| enrofloxacin | BAYTRIL® | 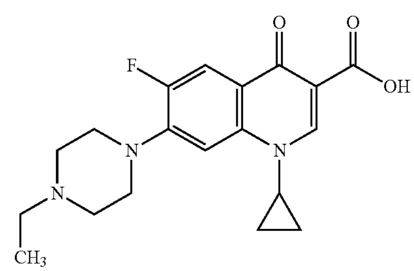 [SMILES: CCN1CCN(c2cc3c(cc2F)c(=O)c(C(=O)O)cn3C2CC2)CC1] |

TABLE 3-continued

Examples of 6-Fluoroquinolin-4(1H)-ones

| 6-Fluoroquinolin-4(1H)-one | Examples of reported trade names for products containing the 6-fluoroquinolin-4(1H)-one | Structure |
|---|---|---|
| fleroxacin | MEGALONE | 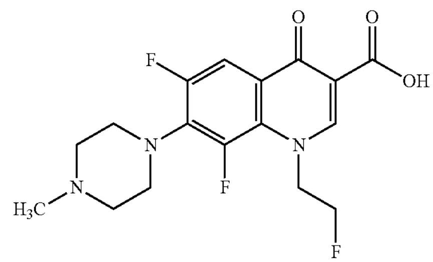 [SMILES: CN1CCN(c2c(F)cc3c(=O)c(C(=O)O)cn(CCF)c3c2F)CC1] |
| flumequine | FLUBACTIN | 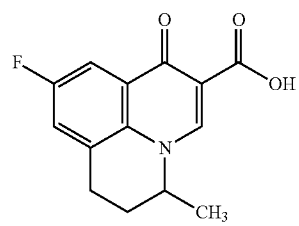 [SMILES: CC1CCc2cc(F)cc3c(=O)c(C(=O)O)cn1c23] |
| garenoxacin | | 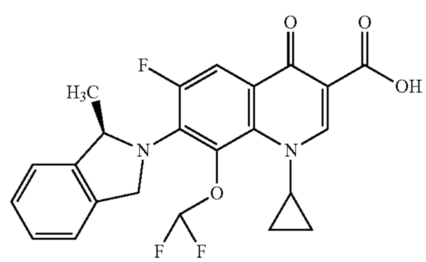 [SMILES: C[C@@H]1c2ccccc2CN1c1c(F)cc2c(=O)c(C(=O)O)cn(C3CC3)c2c1OC(F)F] |
| gatifloxacin | TEQUIN® & ZYMAR® | 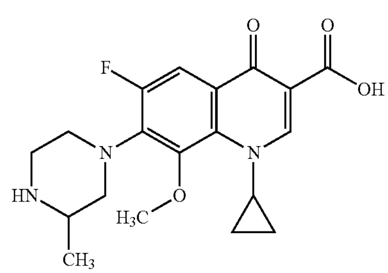 [SMILES: COc1c(N2CCNC(C)C2)c(F)cc2c(=O)c(C(=O)O)cn(C3CC3)c12] |
| grepafloxacin | RAXAR | 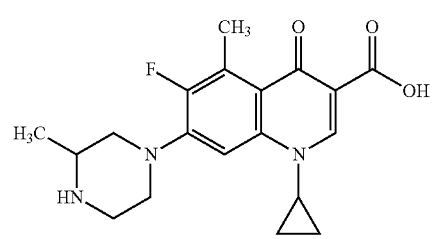 [SMILES: Cc1c(F)c(N2CCNC(C)C2)cc2c1c(=O)c(C(=O)O)cn2C1CC1] |

TABLE 3-continued

Examples of 6-Fluoroquinolin-4(1H)-ones

| 6-Fluoroquinolin-4(1H)-one | Examples of reported trade names for products containing the 6-fluoroquinolin-4(1H)-one | Structure |
|---|---|---|
| ibafloxacin | | 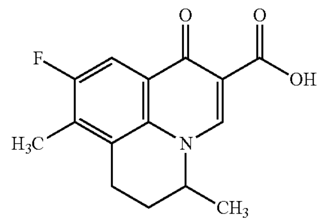 [SMILES: Cc1c(F)cc2c(=O)c(C(=O)O)cn3c2c1CCC3C] |
| levofloxacin | LEVAQUIN®, GATIGOL, TAVANIC, LEBACT, LEVOX, & CRAVIT | 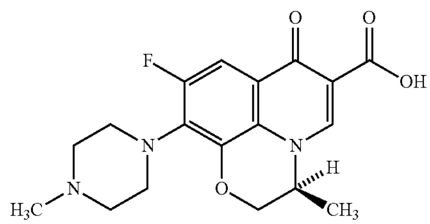 [SMILES: C[C@H]1COc2c(N3CCN(C)CC3)c(F)cc3c(=O)c(C(=O)O)cn1c23] |
| lomefloxacin | MAXAQUIN® | 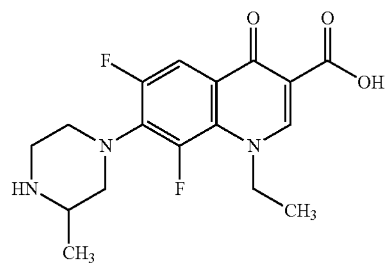 [SMILES: CCn1cc(C(=O)O)c(=O)c2cc(F)c(N3CCNC(C)C3)c(F)c21] |
| marbofloxacin | MARBOCYL® & ZENEQUIN | 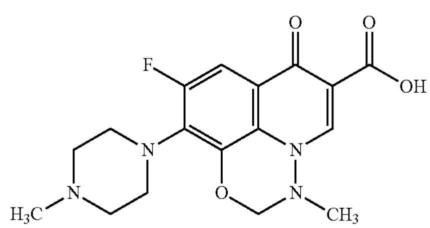 [SMILES: CN1CCN(c2c(F)cc3c(=O)c(C(=O)O)cn4c3c2OCN4C)CC1] |
| moxifloxacin | AVELOX® & VIGAMOX® | 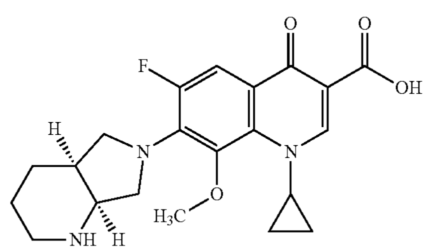 [SMILES: COc1c(N2C[C@@H]3CCCN[C@@H]3C2)c(F)cc2c(=O)c(C(=O)O)cn(C3CC3)c12] |
| nadifloxacin | ACUATIN, NADOXIA, & NADIXA | 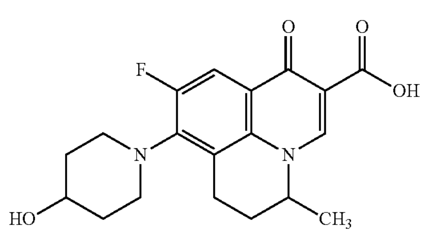 [SMILES: CC1CCc2c(N3CCC(O)CC3)c(F)cc3c(=O)c(C(=O)O)cn1c23] |

TABLE 3-continued

Examples of 6-Fluoroquinolin-4(1H)-ones

| 6-Fluoroquinolin-4(1H)-one | Examples of reported trade names for products containing the 6-fluoroquinolin-4(1H)-one | Structure |
|---|---|---|
| norfloxacin | NOROXIN®, LEXINOR, QUINABIC, & JANACIN | 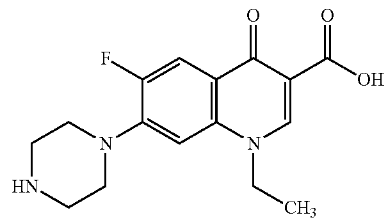 [SMILES: CCn1cc(C(=O)O)c(=O)c2cc(F)c(N3CCNCC3)cc21] |
| ofloxacin | FLOXIN®, OXALDIN, & TARIVID | 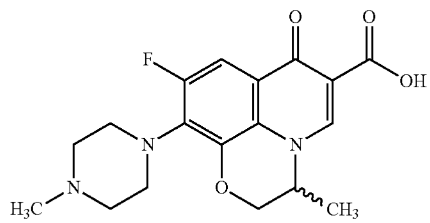 [SMILES: CC1COc2c(N3CCN(C)CC3)c(F)cc3c(=O)c(C(=O)O)cn1c23] |
| orbifloxacin | ORBAX® & VICTAS | 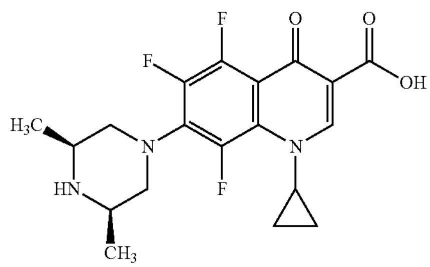 [SMILES: C[C@@H]1CN(c2c(F)c(F)c3c(=O)c(C(=O)O)cn(C4CC4)c3c2F)C[C@H](C)N1] |
| pazufloxacin | | 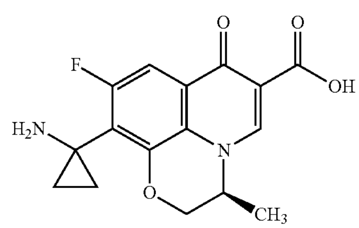 [SMILES: C[C@H]1COc2c(C3(N)CC3)c(F)cc3c(=O)c(C(=O)O)cn1c23] |
| pefloxacin | | 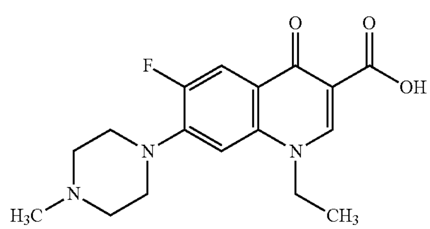 [SMILES: CCn1cc(C(=O)O)c(=O)c2cc(F)c(N3CCN(C)CC3)cc21] |
| pradofloxacin | | 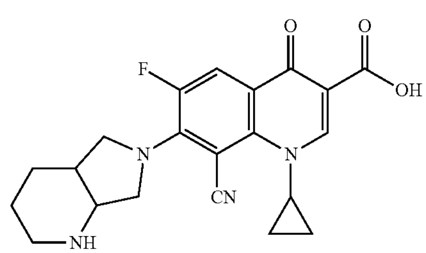 [SMILES: N#Cc1c(N2CC3CCCNC3C2)c(F)cc2c(=O)c(C(=O)O)cn(C3CC3)c12] |

TABLE 3-continued

Examples of 6-Fluoroquinolin-4(1H)-ones

| 6-Fluoroquinolin-4(1H)-one | Examples of reported trade names for products containing the 6-fluoroquinolin-4(1H)-one | Structure |
|---|---|---|
| prulifloxacin | | 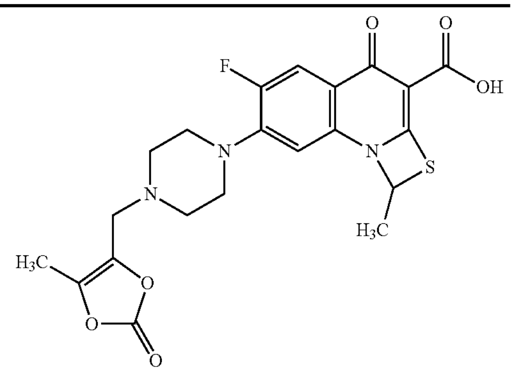 |
| rufloxacin | UROFLOX | 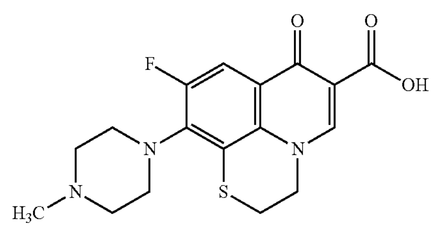 [SMILES: CN1CCN(c2c(F)cc3c(=O)c(C(=O)O)cn4c3c2SCC4)CC1] |
| sarafloxacin | FLOXASOL, SARAFLOX, SARAFIN | 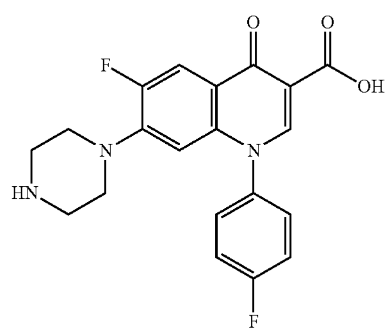 [SMILES: O=C(O)c1cn(-c2ccc(F)cc2)c2cc(N3CCNCC3)c(F)cc2c1=O] |
| sitafloxacin | | 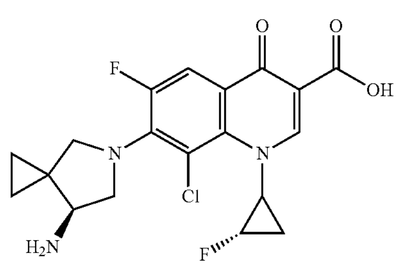 [SMILES: N[C@@H]1CN(c2c(F)cc3c(=O)c(C(=O)O)cn(C4C[C@@H]4F)c3c2Cl)CC12CC2] |
| sparfloxacin | ZAGAM | 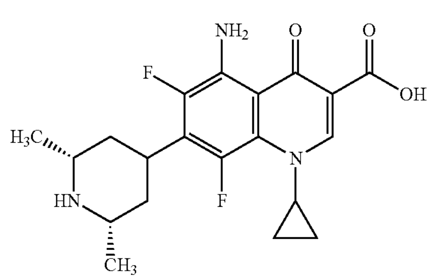 [SMILES: C[C@@H]1CC(c2c(F)c(N)c3c(=O)c(C(=O)O)cn(C4CC4)c3c2F)C[C@H](C)N1] |

TABLE 3-continued

Examples of 6-Fluoroquinolin-4(1H)-ones

| 6-Fluoroquinolin-4(1H)-one | Examples of reported trade names for products containing the 6-fluoroquinolin-4(1H)-one | Structure |
|---|---|---|
| temafloxacin | OMNIFLOX | (structure) |

Other examples of 6-fluoroquinolin-4(1H)-ones include those shown in Table 4:

TABLE 4

Additional Examples of 6-Fluoroquinolin-4(1H)-ones (structures)

TABLE 4-continued

Additional Examples of 6-Fluoroquinolin-4(1H)-ones (structures)

TABLE 4-continued

Additional Examples of 6-Fluoroquinolin-4(1H)-ones

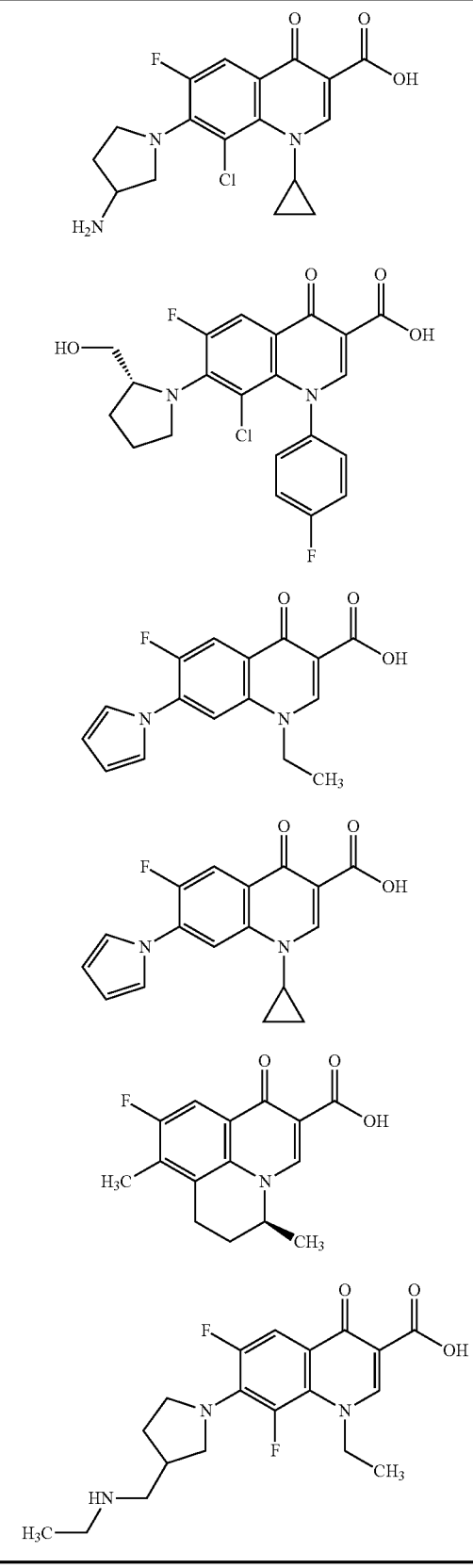

See Chu et al., "Minireview: Structure-Activity Relationships of the Fluoroquinolones," *Antimicrobial Agents and Chemotherapy*, 33(2), pp. 131-135 (February 1989).

In some embodiments, the antibiotic comprises an antibiotic selected from the group consisting of the 6-fluoroquinolin-4(1H)-ones shown in Table 3, salts of such 6-fluoroquinolin-4(1H)-ones, and solvates of such 6-fluoroquinolin-4(1H)-ones and their salts.

In some embodiments, the antibiotic comprises an antibiotic selected from the group consisting of amifloxacin, balofloxacin, ciprofloxacin, clinafloxacin, fleroxacin, garenoxacin, gatifloxacin, grepafloxacin, lomefloxacin, moxifloxacin, norfloxacin, pefloxacin, pradofloxacin, sitafloxacin, sparfloxacin, and temafloxacin; salts of such 6-fluoroquinolin-4(1H)-ones; and solvates of such 6-fluoroquinolin-4(1H)-ones and their salts.

In some embodiments, the antibiotic comprises an antibiotic selected from the group consisting of danofloxacin, difloxacin, enrofloxacin, and sarafloxacin; salts of such 6-fluoroquinolin-4(1H)-ones; and solvates of such 6-fluoroquinolin-4(1H)-ones and their salts.

In some embodiments, the antibiotic comprises an antibiotic selected from the group consisting the 6-fluoroquinolin-4(1H)-ones shown in Table 4, salts of such 6-fluoroquinolin-4(1H)-ones, and solvates of such 6-fluoroquinolin-4(1H)-ones and their salts.

In some embodiments, the antibiotic comprises orbifloxacin, a salt of orbifloxacin, or a solvate of orbifloxacin or an orbifloxacin salt. Orbifloxacin is a known synthetic potent and broad-spectrum antibacterial agent safe and effective for management of diseases, particularly in dogs and cats.

In some embodiments, the antibiotic comprises a 6-fluoroquinolin-4(1H)-one that comprises three rings fused together. In some such embodiments, for example, the antibiotic comprises an antibiotic selected from the group consisting of flumequine, ibafloxacin, levofloxacin, nadifloxacin, ofloxacin, pazufloxacin, prulifloxacin, and rufloxacin; salts of such 6-fluoroquinolin-4(1H)-ones; and solvates of such 6-fluoroquinolin-4(1H)-one and their salts. In other embodiments, the antibiotic comprises marbofloxacin, a salt of marbofloxacin, or a solvate of marbofloxacin or a marbofloxacin salt.

In other embodiments, the antibiotic comprises a naphthyridinone. In general, the naphthyridinone comprises a fluoronaphthyridinone, a salt of the fluoronaphthyridinone, or a solvate of the fluoronaphthyridinone or its salt. Fluoronaphthyridinone antibiotics include, for example, 6-fluoro-1,8-naphthyridin-4(1H)-ones, salts of 6-fluoro-1,8-naphthyridin-4(1H)-ones, and solvates of 6-fluoro-1,8-naphthyridin-4(1H)-ones and their salts. Examples of 6-fluoro-1,8-naphthyridin-4(1H)-ones include those shown in Table 5:

TABLE 5

Examples of 6-Fluoro-1,8-naphthyridin-4(1H)-ones

| 6-Fluoro-1,8-naphthyridin-4(1H)-one | Examples of reported trade names for products containing the 6-fluoro-1,8-naphthyridin-4(1H)-one | Structure |
| --- | --- | --- |
| enoxacin | Penetrex & Enroxil | 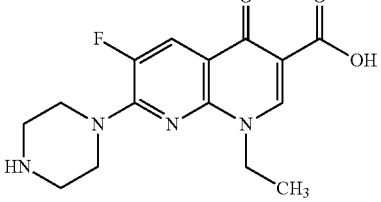 |
| gemifloxacin | Factive | 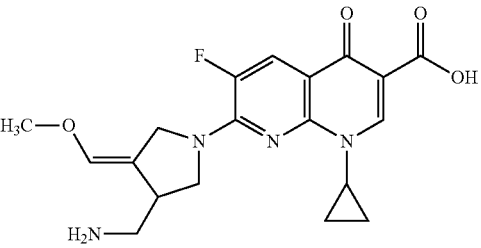 [SMILES: CO/C=C1\CN(c2nc3c(cc2F)c(=O)c(C(=O)O)cn3C2CC2)CC1CN] |
| tosufloxacin |  | 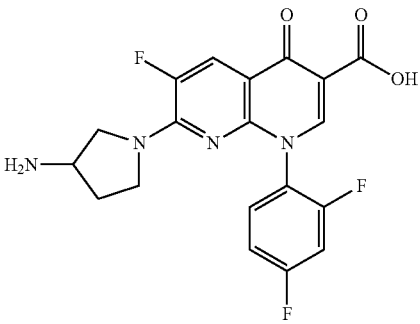 [SMILES: NC1CCN(c2nc3c(cc2F)c(=O)c(C(=O)O)cn3-c2ccc(F)cc2F)C1] |
| trovafloxacin | Trovan | 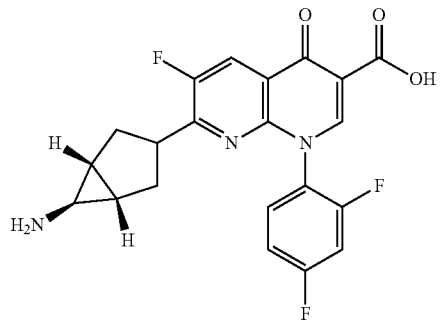 [SMILES: N[C@@H]1[C@H]2CC(c3nc4c(cc3F)c(=O)c(C(=O)O)cn4-c3ccc(F)cc3F)C[C@@H]12] |

In some embodiments, the antibiotic comprises an antibiotic selected from the group consisting of the 6-fluoro-1,8-naphthyridin-4(1H)-ones shown in Table 5, salts of such 6-fluoro-1,8-naphthyridin-4(1H)-ones, and solvates of such 6-fluoro-1,8-naphthyridin-4(1H)-ones and their salts.

In some embodiments, the antibiotic comprises an antibiotic selected from the group consisting of enoxacin, gemifloxacin, tosufloxacin, and trovafloxacin; salts of such 6-fluoro-1,8-naphthyridin-4(1H)-ones; and solvates of such 6-fluoro-1,8-naphthyridin-4(1H)-ones and their salts.

Other examples of 6-fluoro-1,8-naphthyridin-4(1H)-ones include:

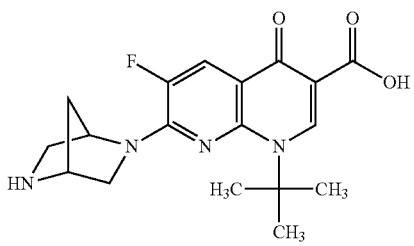 [SMILES: CC(C)(C)n1cc(C(=O)O)c(=O)c2cc(F)c(N3CC4CC3CN4)nc21]

See Chu et al., *Antimicrobial Agents and Chemotherapy*, at p. 132. In some embodiments, the antibiotic comprises this compound, a salt of it, or a solvate of it or its salt.

In general, the antibiotic concentration in the composition is sufficient for the antibiotic to be therapeutically effective at the dose in which the composition is administered. In some embodiments, the antibiotic concentration in the composition (i.e., the total concentration of all antibiotics in the composition) is at least about 0.01% (by weight). In some embodiments, the concentration is from about 0.01 to about 30% (by weight), from about 0.1 to about 10% (by weight), or from about 0.5 to about 5% (by weight).

C. The Organic Acid

The organic acid generally comprises a fatty acid. The fatty acid preferably comprises at least about 3 carbon atoms. In some embodiments, for example, the fatty acid comprises from about 3 to about 18 carbon atoms. In other embodiments, the fatty acid comprises from about 4 to about 18 carbon atoms. In still other embodiments, the fatty acid comprises from about 7 to about 18 carbon atoms.

The fatty acid may be a naturally-occurring fatty acid or a synthetic acid. It also may be saturated or unsaturated. In some embodiments, the fatty acid comprises an unbranched aliphatic chain that comprises at least about 4 carbon atoms, and is either saturated or unsaturated. Preferably, the fatty acid has a melting point that is no greater than about 60° C.

The fatty acid preferably dissolves or is miscible in a vehicle present in the composition at temperatures in which the composition is used. The fatty acid also preferably dissolves or is miscible in a vehicle present in the composition at temperatures in which the composition is stored. Thus, for example, in some embodiments wherein the composition is a suspension comprising a mineral oil vehicle, the fatty acid is miscible in mineral oil at room temperature (i.e., from about 20 to about 25° C.). In such embodiments, the fatty acid also is preferably miscible in mineral oil at cooler or warmer temperatures in which the composition may be used or stored.

In some embodiments, the fatty acid comprises propionic acid (which has 3 carbon atoms). In other embodiments, the fatty acid comprises myristic acid (which has 14 carbon atoms). In other embodiments, the fatty acid comprises lauric acid (which has 14 carbon atoms). In still other embodiments, the fatty acid comprises oleic acid (which has 18 carbon atoms). It should be recognized that the composition can comprise more than one type of fatty acid. For example, in some such embodiments, the composition comprises both oleic acid and lauric acid.

In general, the fatty acid concentration in the composition is sufficient to effectively to reduce (and preferably substantially or completely inhibit) the production of at least one corticosteroid (e.g., mometasone or mometasone furoate) degradation product over at least 1 month, at least 2 months, or at least 5 months while being stored in high density polyethylene ("HDPE") plastic bottles with low density polyethylene ("LDPE") caps at a temperature of at least 15° C., at least 20° C., at least 25° C., at least 40° C. or least at 50° C. In some embodiments, the fatty acid concentration is at least about 0.01% (by weight). In some such embodiments, for example, the concentration is from about 0.01 to about 5.0% (by weight). In other embodiments, the concentration is from about 0.1 to about 2.0% (by weight). In some embodiments, the composition comprises oleic acid, and the oleic acid concentration in the composition is from about 0.1 to about 2.0% (by weight). In other embodiments, the composition comprises lauric acid, and the lauric acid concentration is from about 0.1 to about 1.0% (by weight).

D. Additional Ingredients in the Composition

As noted above, the composition of this invention may (and generally will) comprise other ingredients. Those ingredients may be, for example, one or more other active ingredients and/or one or more excipients.

i. Other Active Ingredients

It is contemplated that a variety of active ingredients may be incorporated into the composition of this invention in addition to the corticosteroid and antibiotic. Any such active ingredient preferably is suitable for the context in which the composition is being used, and not significantly detrimental to the corticosteroid and antibiotic activities.

In some embodiments the composition comprises an antifungal. In some such embodiments, for example, the antifungal comprises an imidazole, a salt of an imidazole, or a solvate of an imidazole or its salt. Imidazoles include, for example, those shown in Table 6:

TABLE 6

Examples of Antifungal Imidazoles

| Imidazole | Examples of reported trade names for products containing the imidazole | Structure |
|---|---|---|
| clotrimazole | CANESTEN®, MYCELEX®, LOTRIMIN®, LOMITRIN AF®, AGISTEN, CLOTRIMADERM, & CLOTRIMAZOLE-TEVA | 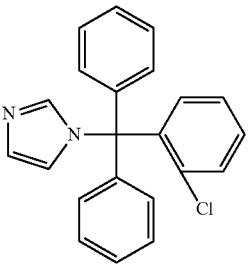 [SMILES: Clc1ccccc1C(c1ccccc1)(c1ccccc1)n1ccnc1] |

TABLE 6-continued
Examples of Antifungal Imidazoles
| Imidazole | Examples of reported trade names for products containing the imidazole | Structure |
|---|---|---|
| econazole | SPECTAZOLE® | 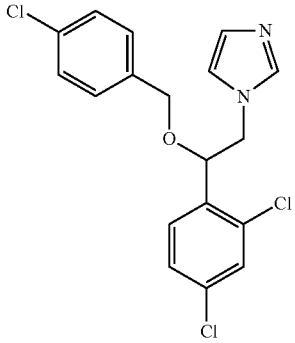 [SMILES: Clc1ccc(COC(Cn2ccnc2)c2ccc(Cl)cc2Cl)cc1] |
| isoconazole | TRAVOGEN | 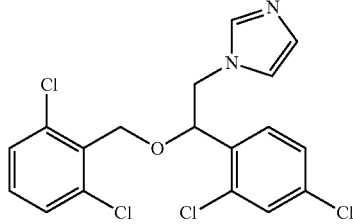 [SMILES: Clc1ccc(C(Cn2ccnc2)OCc2c(Cl)cccc2Cl)c(Cl)c1] |
| ketoconazole | NIZORAL® | 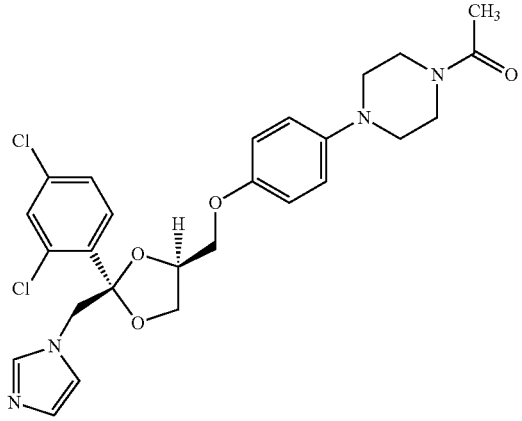 [SMILES: CC(=O)N1CCN(c2ccc(OC[C@H]3CO[C@](Cn4ccnc4)(c4ccc(Cl)cc4Cl)O3)cc2)CC1] |
| myconazole | MONISTAT® | 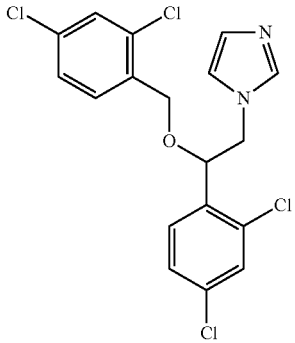 [SMILES: Clc1ccc(COC(Cn2ccnc2)c2ccc(Cl)cc2Cl)c(Cl)c1] |

TABLE 6-continued

Examples of Antifungal Imidazoles

| Imidazole | Examples of reported trade names for products containing the imidazole | Structure |
|---|---|---|
| neticonazole | ATOLANT | 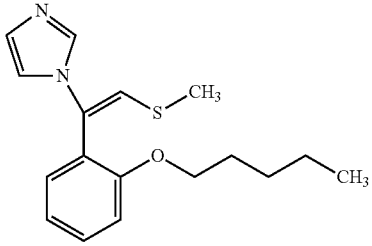 [SMILES: CCCCCOc1ccccc1/C(=C\SC)n1ccnc1] |
| oxiconazole | OXISTAT® | 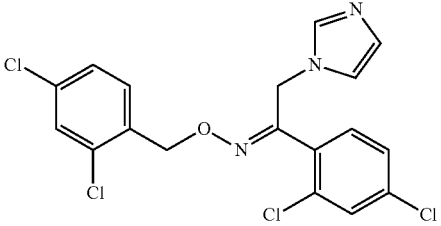 [SMILES: Clc1ccc(CO/N=C(\Cn2ccnc2)c2ccc(Cl)cc2Cl)c(Cl)c1] |
| sertaconazole | ERTACZO® | 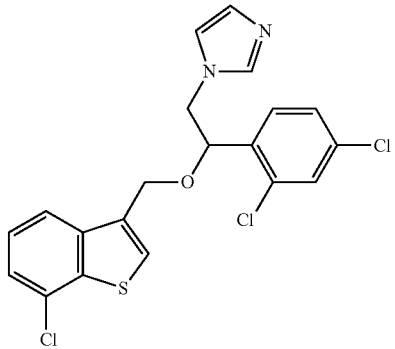 [SMILES: Clc1ccc(C(Cn2ccnc2)OCc2csc3c(Cl)cccc23)c(Cl)c1] |
| sulconazole | EXELDERM® | 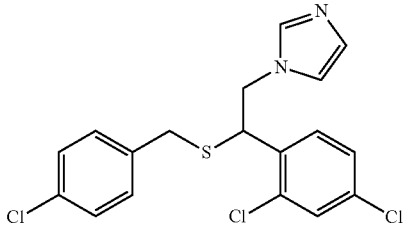 [SMILES: Clc1ccc(CSC(Cn2ccnc2)c2ccc(Cl)cc2Cl)cc1] |
| tioconazole | VAGISTAT® | 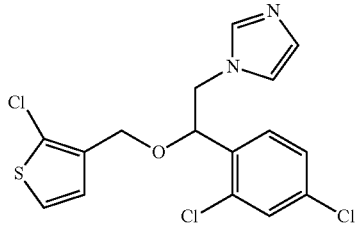 [SMILES: Clc1ccc(C(Cn2ccnc2)OCc2ccsc2Cl)c(Cl)c1] |

In some embodiments, the anti fungal comprises an antifungal selected from the group consisting of the imidazoles shown in Table 6, salts of such imidazoles, and solvates of such imidazoles and their salts.

In other embodiments, the antifungal comprises a triazole, a salt of a triazole, or a solvate of a triazole or its salt.

Triazoles include, for example, those shown in Table 7:

TABLE 7

Examples of Antifungal Triazoles

| Triazole | Examples of reported trade names for products containing the triazole | Structure |
|---|---|---|
| fluconazole | DIFLUCAN® & TRICAN | 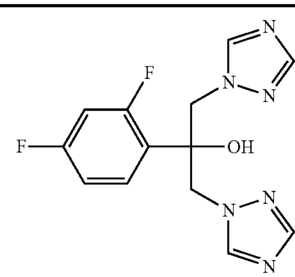 |
| itraconazole | SPORANOX® | 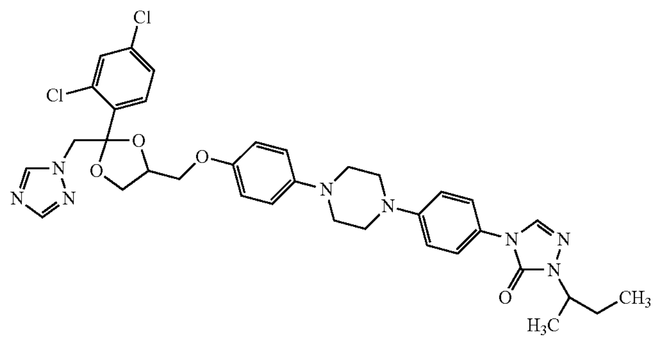 [SMILES: CCC(C)n1ncn(-c2ccc(N3CCN(c4ccc(OCC5COC(Cn6cncn6)(c6ccc(Cl)cc6Cl)O5)cc4)CC3)cc2)c1=O] |
| posaconazole | NOXAFIL® | 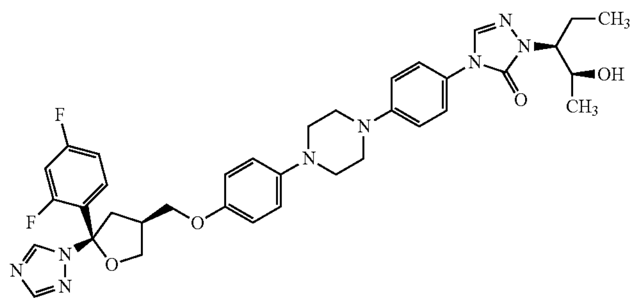 [SMILES: CC[C@@H]([C@H](C)O)n1ncn(-c2ccc(N3CCN(c4ccc(OC[C@H]5CO[C@@](c6ccc(F)cc6F)(n6cncn6)C5)cc4)CC3)cc2)c1=O] |
| saperconazole | | 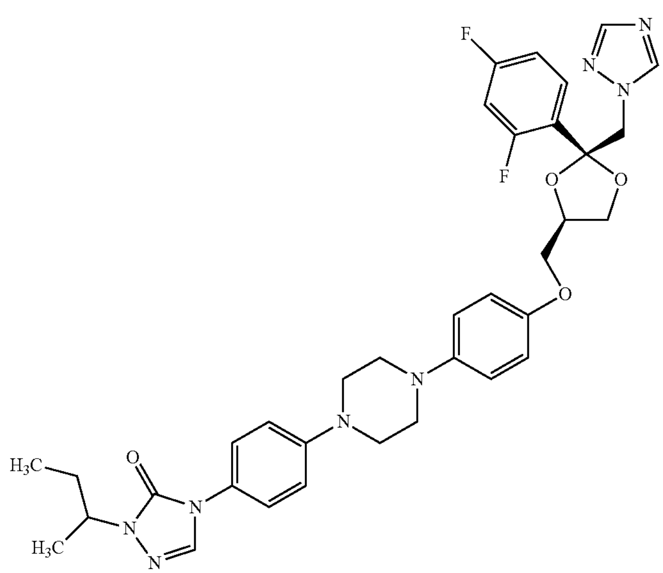 [SMILES: CCC(C)n1ncn(-c2ccc(N3CCN(c4ccc(OC[C@@H]5CO[C@](Cn6cncn6)(c6ccc(F)cc6F)O5)cc4)CC3)cc2)c1=O] |

TABLE 7-continued

Examples of Antifungal Triazoles

| Triazole | Examples of reported trade names for products containing the triazole | Structure |
|---|---|---|
| terconazole | TERAZOL® | 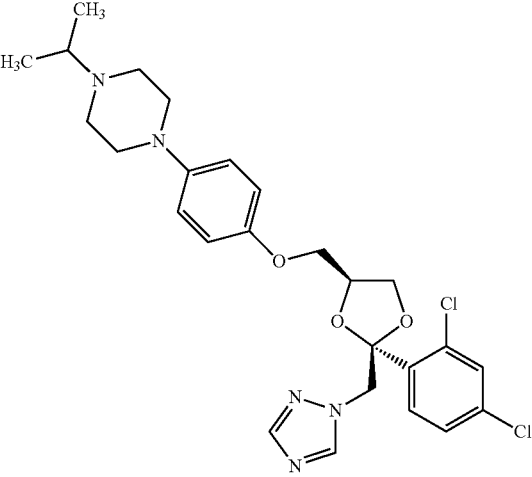 [SMILES: CC(C)N1CCN(c2ccc(OC[C@H]3CO[C@](Cn4cncn4)(c4ccc(Cl)cc4Cl)O3)cc2)CC1] |
| voriconazole | VFEND® | 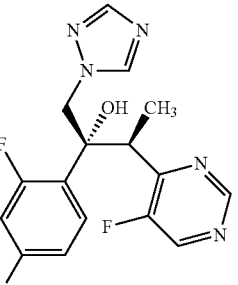 |

In some embodiments, the antifungal comprises an antifungal selected from the group consisting of the triazoles shown in Table 7, salts of such triazoles, and solvates of such triazoles and their salts.

In some embodiments, the antifungal comprises posaconazole, a salt of posaconazole, or a solvate of posaconazole or its salt. In some such embodiments, for example, the antibiotic comprises posaconazole. Posaconazole is known to have antifungal activity against a broad range of fungi, including *Aspergillus, Candida, Cryptococcus, Fusarium*, and other opportunistic fungi. Discussions relating to posaconazole may be found in, for example, U.S. Pat. Nos. 5,661,151; 5,834,472; and 5,846,971.

In some embodiments, the antifungal comprises nystatin, a salt of nystatin, or a solvate of nystatin or a nystatin salt. Nystatin corresponds in structure to:

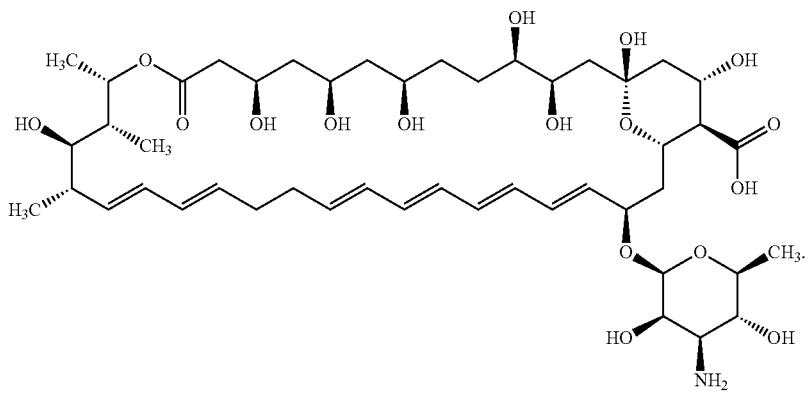

In general, the concentration of antifungal agent in the composition is sufficient for the antifungal agent to be therapeutically effective at the dose in which the composition is administered. When more than one antifungal agent is present in the composition, the total concentration of all the antifungal agents is sufficient for the combined antifungal agents to be therapeutically effective at the dose in which the composition is administered. In some embodiments, the concentration of antifungal agent in the composition (i.e., the total concentration of all antifungal agents in the composition) is at least about 0.01% (by weight). In some such embodiments, for example, the concentration is from about 0.01 to about 1.0% (by weight).

In some embodiments, the composition comprises one or more antibiotics (in addition to the quinolone or naphthyridinone antibiotic(s)). Such antibiotics may include, for example, the following antibiotics (as well as their salts, their solvates, and solvates of their salts):

A. Chloramphenicol, thiamphenicol, and fluorine-containing analogs of chloramphenicol and thiamphenicol (e.g., florfenicol or D-(thrco)-1-p-methylsulfonyl phenyl-2-difluoroacetamido-3-fluoro-1-propanol).

B Tetracyclines, such as chlorotetracycline and oxytetracycline.

C. Amoxicillin, ampicillin, ampicillin trihydrate, ampicillin sodium, apalcillin, aspoxicillin, azlocillin, bacampicillin, carbenicillin, carbenicillin sodium, carfecillin, carindacillin, ciclacillin, cloxacillin sodium, cloxacillin benzathine, dicloxacillin, dicloxacillin sodium, flucloxacillin, hetacillin, lenampicillin, mecillinatn, metampicillin, methicillin, mezlocillin, nafcillin, nafcillin sodium, oxacillin, penicillic acid, penicillin G, penicillin G benzathine, penicillin G potassium, penicillin G sodium, penicillin V, phenethicillin, phenethicillin potassium, piperacillin, piperacillin sodium, pivampicillin, sulbenicillin, sultamicillin, talampicillin, ticarcillin, cefaclor, cefadroxil, cefadroxil monohydrate, cefamandole, cefamandole lithium, cefamandole nanfate, cefamandole sodium, cefazaflur, cefazedone, cefazolin, cefazolin sodium, cefclidine, cefdinir, cefepime, cefetamet, cefixime, cefluprenam, cefinenoxime, cefinetazole sodium, cefodizime, cefonicid, cefoperazone, cefoperazone sodium, ceforanide, cefoselis, cefotaxime, cefotaxime sodium, cefotiam, cefozopran, cefpimizole, cefpimizole sodium, cefpiramide, cefpirome, cefpodoxime, cefprozil, celquinome, cefroxadine, cefsulodin, cefsulodin sodium hydrate, ceftazidime, ceftazidime pentahydrate, ceftezole, ceftibuten, ceftiolene, ceftizoxime, ceftriaxone, ceftriaxone disodium salt, ceftriaxone sodium, cefuroxime, cefuzonam, cephacetrile, cephalexin, cephaloridine, cephalosporin C, cephalothin, cephalothin sodium, cephapirin, cephapirin sodium, cephradine, loracarbef, cefbuperazone, cefoxitin, cefoxitin sodium, cefminox, cefmetazole, cefotetan, either alone or in combination with β-lactamase inhibitors, such as clavulanic acid, potassium clavulanate, sulbactam lodopenicillanic acid, 6-bromopenicillanic acid, olivanic acids, and tazobactam.

D. Macrolide antibiotics, such as azithromycin, brefeldin, clarithromycin, erythromycin, erythromycin estolate, erythromycin ethyl succinate, erythromycin stearate, josamycin, kitasamycin, tulathromycin, and tilmicosin.

In some embodiments, the composition comprises one or more anti-inflammatory ingredients in addition to the corticosteroid(s). Such anti-inflammatory ingredients may include, for example, one or more non-steroidal anti-inflammatory drugs ("NSAIDs"). NSAIDs include, for example, salicylates, arylalkanoic acids, 2-arylpropionic acids (or "profens"), N-acylanthranilic acids, pyrazolidine derivatives, oxicams, COX-2 inhibitors, sulphonanilides, and licofelone. In some embodiments, the NSAID comprises aspirin, ibuprofen, or naproxen. Anti-inflammatory ingredients also may include, for example, antihistamines. Antihistamines include, for example, $H_1$-receptor agonists, $H_2$-receptor agonists, $H_3$-receptor agonists, $H_4$-receptor agonists, mast cell stabilizers, and vitamin C.

ii. Excipients

Contemplated excipients in the compositions of this invention include, for example, liquid vehicles, viscosity-enhancing agents, surfactants, preservatives, stabilizers, resins, fillers, binders, lubricants, glidants, disintegrants, co-solvents, and pharmaceutical-grade dyes or pigments.

In some embodiments, the compositions of this invention are in the form of a suspension. Such compositions generally include a liquid vehicle (or "carrier") such as water, petroleum, animal oils, vegetable oils, mineral oil, or synthetic oil. Physiological saline solution, or glycols (e.g., ethylene glycol, propylene glycol, or polyethylene glycol) also may be included. In some embodiments, the liquid vehicle comprises mineral oil.

Compositions of this invention typically include one or more viscosity-enhancing agents (or "thickening agents"). The concentration of the viscosity-enhancing agent in the composition is generally at least about 0.1% (by weight). For example, in some embodiments, the concentration is from about 0.1 to about 15% (by weight). In some such embodiments, for example, the concentration is from about 0.1 to about 5%. In other embodiments, the concentration is from about 2 to about 10% (by weight), or from about 4 to about 8% (by weight). In some embodiments, the viscosity-enhancing agent comprises polyethylene. Polyethylene is an inert hydrocarbon with a high molecular weight and high melting point. It may be used as a thickening agent to increase the viscosity of, for example, a mineral oil vehicle. In some embodiments, polyethylene is introduced into the composition in the form PLASTIBASE® 50W (commercially available from Bristol-Myers Squibb). PLASTIBASE® 50W contains 5% polyethylene in 95% mineral oil. Other contemplated viscosity-enhancing agents also (or alternatively) may be used. In some embodiments, for example, the viscosity-enhancing agent comprises, for example, methylcellulose, sodium carboxymethylcellulose, hydroxypropyl-methylcellulose, hydroxypropylcellulose, sodium alginate, carbomer, povidone, acacia, guar gum, xanthan gum, or tragacanth. In other embodiments, the viscosity-enhancing agent comprises methylcellulose, carbomer, xanthan gum, guar gum, povidone, sodium carboxymethylcellulose, or magnesium aluminum silicate. In other embodiments, the viscosity-enhancing agent comprises carboxyvinyl polymers; carrageenan; hydroxyethyl cellulose; laponite; and water soluble salts of cellulose ethers, such as sodium carboxymethylcellulose and sodium carboxymethyl hydroxyethyl cellulose. In still other embodiments, the viscosity-enhancing agent comprises natural gums, such as gum karaya, xanthan gum, gum arabic, and gum tragacanth. In still yet other embodiments, the viscosity-enhancing agent comprises colloidal magnesium aluminum silicate or finely divided silica, which can be used as part of the thickening agent to further improve texture. In still yet further embodiments, the viscosity-enhancing agent comprises homopolymers of acrylic acid crosslinked with an alkyl ether of pentaerythritol or an alkyl ether of sucrose, or carbomers. Carbomers are commercially available from B.F. Goodrich as the CARBOPOL® series. In some embodiments, the carbomer is CARBOPOL® 934, 940, 941, 956, or a mixture thereof. Copolymers of lactide and glycolide monomers may be useful for delivery of actives, particularly where the copolymer has a molecular weight in the range of from about 1,000 to about 120,000 (number average). These polymers are described in U.S. Pat. Nos. 5,198,220; 5,242,910; and 4,443,430.

Contemplated surfactants include, for example, polyoxyethylene sorbitan fatty acid esters; polyoxyethylene monoalkyl ethers; sucrose monoesters; lanolin esters and ethers; alkyl sulfate salts; and sodium, potassium, and ammonium salts of fatty acids.

Contemplated preservatives include, for example, phenol; alkyl esters of parahydroxybenzoic acid (e.g., methyl p-hydroxybenzoate (or "methylparaben") and propyl p-hydroxybenzoate (or "propylparaben")); sorbic acid; o-phenylphenol benzoic acid and the salts thereof; chlorobutanol; benzyl alcohol; thimerosal; phenyl mercuric acetate and nitrate; nitromersol, benzalkonium chloride; and cetylpyridinium chloride. A particularly contemplated preservative is sorbic acid. To the extent a composition of this invention comprises a preservative, the preservative concentration in the composition generally is no greater than about 5% (by weight). In some embodiments, for example, the preservative concentration is from about 0.01 to about 5% (by weight).

Contemplated stabilizers include, for example, chelating agents, such as edetate sodium. Contemplated stabilizers also include, for example, antioxidants, such as butylated hydroxyanisole and sodium monothioglycerol.

Contemplated binders include, for example, gelatin, acacia, and carboxymethyl cellulose.

Contemplated lubricants include, for example, magnesium stearate, stearic acid, and talc.

Contemplated disintegrants include, for example, corn starch and alginic acid.

Other inert ingredients may generally be added to the composition as desired. It is contemplated that these may include, for example, lactose, mannitol, sorbitol, calcium carbonate, sodium carbonate, tribasic calcium phosphate, dibasic calcium phosphate, sodium phosphate, kaolin, compressible sugar, starch, calcium sulfate, dextro or microcrystalline cellulose, colloidal silicon dioxide, starch, sodium starch glycolate, crospovidone, croscarmellose sodium, microcrystalline cellulose, tragacanth, hydroxypropylcellulose, pregelatinized starch, povidone, ethylcellulose, hydroxypropylcellulose, hydroxypropylmethylcellulose, and methylcellulose.

E. Salts

As noted above, many compounds present in the composition of this invention may be in the form of a salt. For example, many of the above-described antibiotics, corticosteroids, and antifungals may be in the form of a salt. A salt may be advantageous due to one or more of its physical properties, such as pharmaceutical stability in differing temperatures and humidities; crystalline properties; and/or a desirable solubility in water, oil, or other solvent. Acid and base salts typically can be formed by, for example, mixing a compound with an acid or base, respectively, using various known methods in the art. In general, when the composition of this invention is intended to be administered in vivo (i.e., to an animal) for a therapeutic benefit, all the salts in the composition preferably are pharmaceutically acceptable.

An acid addition salt typically can be prepared by reacting a free base compound with an approximately stoichiometric amount of an inorganic or organic acid. Examples of often suitable inorganic acids for making pharmaceutically acceptable salts include hydrochloric, hydrobromic, hydroiodic, nitric, carbonic, sulfuric, and phosphoric acid. Examples of often suitable organic acids for making pharmaceutically acceptable salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalensulfonic, oxalic, palmoic, pectinic, 3-phenylpropionic, picric, pivalic, thiocyanic, tosylic, and undecanoic acid.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

II. Preparation of the Compositions of this Invention

The compositions of this invention generally may be prepared using, for example, techniques well-known in the art. Typically, any vehicle(s) to be used in the composition (or a portion of such vehicle(s)) is/are added to a compounding vessel, followed by the remaining excipients, the actives, and the fatty acid. In general, the order in which the components are added to the vessel is not critical.

III. Treatment Methods Using a Composition of this Invention

Compositions of this invention may generally be used to treat infections in animals. It is contemplated that the composition may be used to treat a range of animals, especially mammals. Such mammals include, for example, humans. Other mammals include, for example, farm or livestock mammals (e.g., swine, bovines, sheep, goats, etc.), laboratory mammals (e.g., mice, rats, birds, etc.), companion mammals (e.g., dogs, cats, equines, etc.), and wild and zoo mammals (e.g., buffalo, deer, etc.). In some embodiments, the compositions are used to treat canines (e.g., dogs). In other embodiments, the compositions are used to treat felines (e.g., domestic cats). It is contemplated that the compositions also are suitable to treat non-mammals, such as birds (e.g., turkeys, chickens, etc.) and fish (e.g., salmon, trout, koi, etc.).

In general, the compositions of this invention are administered in a dosage form that provides a therapeutically effective amount of the composition (and particularly the active ingredients) to the infection site. For an anti-inflammatory (e.g., a corticosteroid, such as mometasone furoate monohydrate), a "therapeutically effective amount" is an amount that is sufficient to ameliorate, suppress, or eradicate target inflammation, or effect antipruritic or vasoconstrictive action in a target tissue. For an anti-infective (e.g., an antibiotic or antifungal), a "therapeutically effective amount" is an amount that is sufficient to ameliorate, suppress, or eradicate a target pathogen infection. In some embodiments, a sufficient amount of the composition is administered to achieve an antibiotic concentration that is at least equal to the $MIC_{90}$ level (minimum inhibitory concentration, i.e., the concentration that inhibits the growth of 90% of the target pathogen) of the antibiotic for a target pathogen. To the extent the composition comprises multiple active ingredients having combined effects on a desired target tissue or pathogen, the amount of each ingredient that constitutes a "therapeutically effective amount" is the amount that, when combined with the other active ingredients, causes the desired effect on the target tissue or pathogen.

It is contemplated that the compositions of this invention may be administered rectally, vaginally, via inhalation (e.g., via a mist or aerosol), transdermally (e.g., via a transdermal patch), or parenterally (e.g., subcutaneous injection, intravenous injection, intramuscular injection, etc.). It also is contemplated that the compositions may be administered orally. For example, the composition may be added to the intended animal recipient's feed, either directly or as part of a premix; or as a separate dosage form.

In some embodiments, a composition of this invention is used to treat an otic infection. In some such embodiments, the otic infection is in a dog. In other embodiments, the otic infection is in a cat. When used to treat an otic infection, the composition of this invention is typically administered to the animal's infected ear(s). Although a single daily dose is preferred, it is contemplated that the composition can be administered in multiple daily doses. In many instances, one dose is sufficient to treat the infection, particularly when the composition comprises, for example, mometasone furoate monohydrate, orbifloxacin, and posaconazole. In some circumstances, however, it may be desirable (or necessary) to administer a second dose at, for example, 48 hours after the first dose to completely treat the animal (or ensure that the treatment is complete). In other instances, the composition may be administered daily for up to 7 days (or more).

Determining the proper dosage is generally within the skill in the art. The precise dose will depend on various factors. These factors may include, for example, the type (e.g., species and breed), age, size, sex, diet, activity, and condition of the intended recipient; pharmacological considerations, such as the activity, efficacy, pharmacokinetic, and toxicology profiles of the particular composition administered; and whether the composition is being administered as part of a combination therapy with one or more active ingredients. For example, in some embodiments wherein a composition of this invention is used to treat an otic infection in a dog, the dose is from about 1 to about 10 drops. In other embodiments wherein a composition of this invention is used to treat an otic infection in a dog, the dose is from about 25 to about 500 mg. In some such embodiments, for example, the dose is from about 25 to about 250 mg.

IV. Therapeutic Kits

This invention also is directed to kits that are, for example, suitable for use in performing the treatment methods described above. In general, such a kit will comprise a therapeutically effective amount of a composition of this invention, and an additional component(s). The additional component(s) may be, for example, one or more of the following: a diagnostic tool, instructions for administering the composition, or an apparatus for administering the composition (e.g., a syringe or squeeze bottle). In some embodiments for otic treatments, the kit may comprise a composition of this invention in combination with, for example, an apparatus for cleaning an ear and/or an ear-cleaning solution. Examples of contemplated apparatuses for cleaning an ear include cleaning cloths (e.g., dry cloths or alcohol pads) or a powered ear cleaner (such as the AURIFLUSH® System sold by Schering-Plough Corp.). Examples of contemplated ear-cleaning solutions include Virbac Animal Health's CERULYTIC® Solution (comprising propylene glycol dicaprylate/dicaprate, benzyl alcohol, fragrance, and butylated hydroxytoluene), Pfizer Inc.'s OTI-CLENS® Solution (comprising propylene glycol-malic acid, benzoic acid, and salicylic acid), Vet Solutions Ear Cleaning Solution (comprising propylene glycol, aloe vera gel, Sd alcohol 40-2, lactic acid, glycerin, dioctyl sodium sulfosuccinate, salicylic acid, fragrance, benzoic acid, and benzyl alcohol), and IVX Animal Health's OTIRINSE® Solution (comprising dioctyl sodium sulfosuccinate, salicylic acid, lactic acid, benzoic acid, and aloe vera).

EXAMPLES

The following examples are merely illustrative, and not limiting to the remainder of this disclosure in any way.

Example 1. Stabilization of a Suspension Using Oleic Acid or Lauric Acid

The purpose of this experiment was to demonstrate that oleic acid or lauric acid can reduce the formation of at least one mometasone degradation product in a suspension comprising mometasone furoate monohydrate in combination with orbifloxacin. In this experiment, the suspension had the composition shown in Table 8:

TABLE 8

Suspension Comprising a Mometasone Compound and a Fluoroquinolone Antibiotic

| Component | Concentration (mg/g) |
| --- | --- |
| Micronized Orbifloxacin | 10.0 |
| Micronized Mometasone Furoate Monohydrate | 1.0 |
| Micronized Posaconazole | 1.0 |
| Mineral Oil | 685.0 |
| Plasticized Hydrocarbon Gel-Ointment Base (Plasticbase 50W) | quantity sufficient to bring the total mass to 1 g (after any addition of oleic acid or lauric acid) |

The suspension was separated into sub-lots. Each sub-lot was combined with oleic acid to achieve a specific oleic acid concentration (at 0.1%, 0.2%, 0.5%, 1.0%, or 2.0%), combined with lauric acid to achieve a specific lauric acid concentration (0.1%, 0.2%, 0.5%, or 1.0%), or combined with no oleic or lauric acid (i.e., the controls). The sub-lots were packaged into 7.5 g HDPE plastic bottles with LDPE caps, and then placed on stability storage in the upright position. To avoid introducing any contaminants from labels, none of the packages contained a commercial label. Each of the bottles was stored under one of the following set of conditions (a) a temperature of 40° C. and a relative humidity of 75%, or (b) 50° C. under ambient conditions.

Samples were evaluated with HPLC at the beginning of the experiment, and then at the 1-month, 2-month, and 5-month time points afterward to determine the concentration of the mometasone degradation product. The observed concentrations of the mometasone degradation product are shown in Table 9:

TABLE 9

Mometasone Degradation Product Concentration Observed Over Time Under Different Conditions and Different Oleic Acid and Lauric Acid Concentrations

| | | Time Points (months) and Conditions | | | | | |
|---|---|---|---|---|---|---|---|
| Acid Added | Initial | 1 40° C. 75% RH | 1 50° C. Ambient | 2 40° C. 75% RH | 2 50° C. Ambient | 5 40° C. 75% RH | 5 50° C. Ambient |
| Control (none) | ND | 0.35% | 0.26% | 0.46% | 0.30% | 0.60% | 0.25% |
| 0.1% Oleic Acid | ND | ND | ND | ND | ND | ND | ND |
| 0.2% Oleic Acid | ND | ND | ND | ND | ND | ND | ND |
| 0.5% Oleic Acid | ND | ND | ND | ND | ND | ND | ND |
| 1.0% Oleic Acid | ND | ND | ND | ND | ND | ND | ND |
| 2.0% Oleic Acid | ND | ND | ND | ND | ND | ND | ND |
| 0.1% Lauric Acid | ND | ND | ND | ND | ND | ND | ND |
| 0.2% Lauric Acid | ND | ND | ND | ND | ND | ND | ND |
| 0.5% Lauric Acid | ND | ND | ND | ND | ND | ND | ND |
| 1.0% Lauric Acid | ND | ND | ND | ND | ND | ND | ND |

In Table 9, "ND" means none detected. As can be seen, the presence of both acids at all the tested levels inhibited the formation of the mometasone degradation product for up to 5 months at 40° C. and 75% relative humidity, and at 50° C. under ambient conditions. Applicants also did not observe any changes in the physical appearance of the samples, and did not detect any new degradation products as a result of the oleic acid or lauric acid being added.

Example 2. An Illustrative Otic Formulation Comprising Oleic Acid

The following Table 10 illustrates a composition of this invention comprising oleic acid.

TABLE 10

Illustrative otic Formulation Comprising Oleic Acid

| Component | Concentration (mg/g) |
|---|---|
| Micronized Orbifloxacin | 10.0 |
| Micronized Mometasone Furoate Monohydrate | 1.0 |
| Micronized Posaconazole | 1.0 |
| Mineral Oil | 685.0 |
| Oleic Acid | 20 |
| Plasticized Hydrocarbon Gel-Ointment Base (Plasticbase 50W) | quantity sufficient to bring the total mass to 1 g |

Example 3. An Illustrative Otic Formulation Comprising Lauric Acid

The following Table 11 illustrates a composition of this invention comprising lauric acid.

TABLE 11

Illustrative otic Formulation Comprising Oleic Acid

| Component | Concentration (mg/g) |
|---|---|
| Micronized Orbifloxacin | 10.0 |
| Micronized Mometasone Furoate Monohydrate | 1.0 |
| Micronized Posaconazole | 1.0 |
| Mineral Oil | 685.0 |
| Lauric Acid | 20 |
| Plasticized Hydrocarbon Gel-Ointment Base (Plasticbase 50W) | quantity sufficient to bring the total mass to 1 g |

The words "comprise", "comprises", and "comprising" are to be interpreted inclusively rather than exclusively. This interpretation is intended to be the same as the interpretation that these words are given under United States patent law.

The term "pharmaceutically acceptable" is used adjectivally to mean that the modified noun is appropriate for use in a pharmaceutical product. When it is used, for example, to describe a salt or excipient, it characterizes the salt or excipient as being compatible with the other ingredients of the composition, and not deleterious to the intended recipient animal to the extent that the deleterious effect(s) outweighs the benefit(s) of the salt or excipient.

All references cited in this patent are incorporated by reference into this patent.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A stabilized pharmaceutical composition comprising: a corticosteroid wherein the corticosteroid is Mometasone, mometasone furoate or mometasone furoate monohydrate, an antibiotic, wherein the antibiotic is orbifloxacin, an antifungal agent wherein the antifungal agent is posaconazole, a fatty acid, wherein the fatty acid is lauric acid in an amount of about 0.1 to about 1.0% by weight or oleic acid in an amount of about 0.1 to about 2.0% by weight, and mineral oil, wherein the formation of mometasone degradation products is inhibited in the composition when the composition is stored at room temperature or greater over an extended time, wherein, the mometasone, mometasone furoate or mometasone furoate monohydrate is in an amount of about 1.0% by weight, the orbifloxacin is in an amount of about 10.0% by weight, and the posaconazole is in an amount of about 1.0% by weight.

2. The composition of claim 1, wherein the composition is stored at 40° C. and 75% relative humidity.

3. The composition of claim 1, wherein the composition is stored at 50° C. and ambient conditions.

4. The composition of claim 1, wherein the extended time is 5 months.

5. The composition of claim 1, wherein the extended time is 2 months.

6. The composition of claim 1, wherein the extended time is 1 month.

7. A method for stabilizing a pharmaceutical composition by inhibiting the formation of corticosteroid degradation products, comprising combining with the pharmaceutical composition a fatty acid, wherein the fatty acid is lauric acid in an amount of about 0.1 to about 1.0% by weight or oleic acid in an amount of about 0.1 to about 2.0% by weight, wherein the pharmaceutical composition comprises a corticosteroid selected from the group consisting of mometasone, mometasone furoate, and mometasone furoate monohydrate, an antibiotic, wherein the antibiotic is orbifloxacin, an antifungal agent wherein the antifungal agent is posaconazole and mineral oil, wherein, the mometasone, mometasone furoate or mometasone furoate monohydrate is in an amount of about 1.0% by weight, the orbifloxacin is in an amount of about 10.0% by weight, and the posaconazole is in an amount of about 1.0% by weight and wherein the formation of mometasone degradation products is inhibited in the composition when the composition is stored at room temperature or greater over an extended time.

8. The method of claim 7, wherein the composition is stored at 40° C. and 75% relative humidity.

9. The method of claim 7, wherein the composition is stored at 50° C. and ambient conditions.

10. The method of claim 7, wherein the extended time is 5 months.

11. The method of claim 7, wherein the extended time is 2 months.

12. The method of claim 7, wherein the extended time is 1 month.

* * * * *